United States Patent
Fraley et al.

(10) Patent No.: US 6,349,025 B1
(45) Date of Patent: Feb. 19, 2002

(54) LEAK TESTABLE CAPACITIVE FILTERED FEEDTHROUGH FOR AN IMPLANTABLE MEDICAL DEVICE

(75) Inventors: Mary A. Fraley, Minnetonka; Ronald F. Hoch, Andover; Dale W. Schak, Maplewood; Lynn M. Seifried, Minneapolis; William D. Wolf, St. Louis Park, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/696,601

(22) Filed: Oct. 25, 2000

Related U.S. Application Data

(60) Provisional application No. 60/168,118, filed on Nov. 30, 1999, now abandoned.

(51) Int. Cl.[7] .................................................. H01G 4/35
(52) U.S. Cl. ..................................... 361/302; 361/306.1
(58) Field of Search .................................. 361/302, 303, 361/306.1, 309, 306.3; 333/182, 183, 184

(56) References Cited

U.S. PATENT DOCUMENTS

| | | | |
|---|---|---|---|
| 4,420,652 A | 12/1983 | Ikeno | |
| 4,424,551 A | * 1/1984 | Stevenson et al. | 361/302 |
| 4,991,582 A | 2/1991 | Byers et al. | |
| 5,287,076 A | 2/1994 | Johnescu et al. | |
| 5,333,095 A | * 7/1994 | Stevenson et al. | 361/302 |
| 5,434,358 A | 7/1995 | Glahn et al. | |
| 5,470,345 A | 11/1995 | Hassler et al. | |
| 5,620,476 A | 4/1997 | Truex et al. | |
| 5,650,759 A | * 7/1997 | Hittman et al. | 333/182 |
| 5,683,435 A | 11/1997 | Truex et al. | |
| 5,685,632 A | 11/1997 | Schaller et al. | |
| 5,735,884 A | 4/1998 | Thompson et al. | |
| 5,750,926 A | 5/1998 | Schulman et al. | |
| 5,759,197 A | 6/1998 | Sawchuk et al. | |
| 5,782,891 A | 7/1998 | Hassler et al. | |
| 5,836,992 A | 11/1998 | Thompson et al. | |
| 5,866,851 A | 2/1999 | Taylor et al. | |
| 5,867,361 A | 2/1999 | Wolf et al. | |
| 5,870,272 A | 2/1999 | Seifried et al. | |
| 5,896,267 A | 4/1999 | Hittman et al. | |
| 5,905,627 A | * 5/1999 | Brendel et al. | 361/302 |
| 5,959,829 A | 9/1999 | Stevenson et al. | |
| 5,973,906 A | 10/1999 | Stevenson et al. | |
| 5,999,398 A | * 12/1999 | Makl et al. | 361/302 |

* cited by examiner

Primary Examiner—Anthony Dinkins
(74) Attorney, Agent, or Firm—Girma Wolde-Michael

(57) ABSTRACT

A filtered feedthrough that does not block passage of gas in a helium leak test and enables testing of the hermeticity of the feedthrough while inhibiting high voltage arcing is disclosed in single filtered feedthrough and multiple filtered feedthrough array configurations. Each filtered feedthrough comprises a ferrule, an insulator, a feedthrough pin, a filter element, and a pre-formed insulative barrier or spacer located in an interior space between the feedthrough insulator and the filter element rather than a non-conductive adhesive filling the interior space. A gas flow path or pathway extends from the interior space to the exterior of the feedthrough bypassing each filter element. Any leak test gas applied in a hermeticity test and passing through defects in the feedthrough insulator or its attachment to the feedthrough pin or ferrule enters the interior space. The gas pathway extends from an interior space through one or more side wall hole of the ferrule and/or through one or more gap between the ferrule interior surface and the outer surface of the filter element.

22 Claims, 7 Drawing Sheets

LEAK TESTABLE CAPACITIVE FILTERED FEEDTHROUGH FOR AN IMPLANTABLE MEDICAL DEVICE

This application claims priority and benefits from Provisional Patent Application No. 60/168,118, filed Nov. 30, 1999 now abandoned entitled LEAK TESTABLE IPG/ICD FILTER FEEDTHROUGH ATTACHMENT.

FIELD OF THE INVENTION

This invention relates to electrical feedthroughs of improved design and to their method of fabrication, particularly for use with implantable medical devices.

BACKGROUND OF THE INVENTION

Electrical feedthroughs serve the purpose of providing an electrical circuit path extending from the interior of a hermetically sealed case or housing to an external point outside the case or housing. Implantable medical devices (IMDs) such as implantable pulse generators (IPGs) for cardiac pacemakers, implantable cardioverter/defibrillators (ICDs), nerve, brain, organ and muscle stimulators and implantable monitors, or the like, employ such electrical feedthroughs through their housing to make electrical connections with leads, electrodes and sensors located outside the housing.

Such feedthroughs typically include a ferrule adapted to fit within an opening in the housing, one or more conductor, and a non-conductive, low bulk permeability, insulator which supports and electrically isolates each such conductor from any other conductors passing through it and from the ferrule. Each conductor typically comprises electrical wire or pin that extends through a hole extending through the insulator. The insulator is typically formed of glass, sapphire or ceramic materials and is either glassed or brazed to the ferrule and each pin and provides a hermetic seal to prevent entry of body fluids through the feedthrough and into the housing of the IMD. The IMD housing is typically formed of a biocompatible metal, e.g., titanium, although non-conductive ceramic materials have been proposed for forming the housing. The ferrule is typically of a metal that can be welded or otherwise joined to the housing in a hermetically sealed manner. Such feedthroughs are shown in commonly assigned U.S. Pat. Nos. 4,991,582, 5,782,891, and 5,866,851 and in U.S. Pat. No. 5,470,345. It has also been proposed to use co-fired ceramic layer substrates that are provided with conductive pathways formed of traces and vias as disclosed, for example, in U.S. Pat. Nos. 4,420,652, 5,434,358, 5,782,891, 5,620,476, 5,683,435, 5,750,926, and 5,973,906.

Such single and multi-conductor feedthroughs have an internally disposed portion configured to be disposed inside the housing for connection with electrical circuitry and an externally disposed portion configured to be disposed outside the housing. Each externally disposed portion of a feedthrough pin is coupled electrically with a connector element for making connection with leads, electrodes, sensors or other components.

Many of the aforementioned IMDs include elongated electrical medical leads having one or more lead conductor connected at its proximal end to a connector. The elongated lead conductor together with conductive connector and feedthrough components within the connector effectively act as an antenna that tend to pick up stray electromagnetic interference (EMI) signals. At certain frequencies, such EMI can interfere with normal IMD operations, e.g., by being mistaken for telemetry signals and cause an IMD to change an operating mode or parameter.

This problem has been addressed in certain of the above-referenced patents by incorporating a capacitor structure upon the internally facing portion of the feedthrough ferrule coupled between each feedthrough conductor and a common ground, the ferrule, to filter out any high frequency EMI transmitted from the external lead conductor through the feedthrough conductor. The feedthrough capacitors originally were discrete capacitors but presently can take the form of chip capacitors that are mounted as shown in the above-referenced '891, '345, '476, and '906 patents and in further U.S. Pat. Nos. 5,650,759, 5,896,267 and 5,959,829, for example. Or the feedthrough capacitors can take the form of discrete discoidal capacitive filters or discoidal capacitive filter arrays as shown in commonly assigned U.S. Pat. Nos. 5,735,884, 5,759,197, 5,836,992, 5,867,361, and 5,870,272 and further U.S. Pat. Nos. 4,424,551, 5,287,076, 5,333,095, 5,905,627 and 5,999,398. The electrical poles of such discoidal capacitive filters are soldered, epoxied or otherwise adhered between a feedthrough pin and the ferrule such that the discoidal filter fills the space between the ferrule and pin or pins.

After fabrication, all such feedthroughs are subjected to helium leak testing to determine whether minute leaks have occurred through defects caused by the stresses induced in handling, fitting, and brazing or glassing the components together. Helium leak testing is also conducted after the feedthrough is attached, typically by welding, to the IMD housing to detect any defects caused by the attachment process. A high integrity hermetic seal for IMD applications is very critical to prevent the ingress of body fluid vapors into the IMD housing. Even an extremely small leak rate of body fluids through or around the insulator can, over a period of many years, build up fluids that damage sensitive internal electronic components and that can cause catastrophic failure of the IMD.

When a discoidal capacitive filter is attached across the ferrule and the pin, it becomes difficult to detect any leaks through or around the insulator due to the adhesion of the discoidal capacitive filter to the ferrule and pin and due to use of a polymeric adhesive to fill the space between the facing inner end surfaces of the discoidal capacitive filter and the annular insulator. It becomes difficult to detect any helium that passes through a crack or defect in or around the insulator because the rate of helium gas passage is diminished by the polymeric adhesives filling the space and adhering the discoidal capacitive filter to the ferrule and pin.

In low voltage capacitive filtered feedthroughs or feedthrough arrays shown in the above-referenced '361 patent, the space between the inner end surfaces of the discoidal capacitive filters and the insulator can be left empty, because electrical arcing between the feedthrough pin and the discoidal capacitive filter outer surface (typically the ground termination) does not take place.

Such an approach is not practical for high voltage capacitive filtered feedthroughs used in ICDs which conduct high voltage defibrillation shocks, for example, where the space between the inner end surfaces of the discoidal capacitive filters and the insulator are filled with epoxy to inhibit electrical arcing.

SUMMARY OF THE INVENTION

A filtered feedthrough is provided in accordance with the present invention that does not block passage of gas in a helium leak test and enables testing of the hermeticity of the feedthrough while providing insulation of the inner surface of the filter element from the feedthrough pin and ferrule. The present invention is realized in single pin filtered feedthroughs comprising a single discrete filter element coupled between the feedthrough pin and the ferrule and in filtered feedthrough arrays or multi-polar filtered feedthroughs comprising a plurality of filter elements coupled between a respective plurality of feedthrough pins and the ferrule.

The filtered feedthrough of the present invention preferably provides a pre-formed insulative barrier or spacer located between the feedthrough insulator and the filter element rather than use of non-conductive potting compound that blocks gas passage. The pre-formed insulative barrier or spacer restrains the flow of adhesive applied into the space between the lower surface of the filter element and the spacer during attachment of the filter element to the feedthrough pin and ferrule. Thus, an air space is maintained between the insulator and the pre-formed insulative barrier or spacer that leak test gas passing through defects in the insulator or the braze between the insulator and the ferrule or the pin can enter.

The gas bypass pathway preferably extends from the air space and further comprises one of one or more air gap bypassing the filter element or one or more pin hole through the ferrule wall at one or more location remote from the weldment with the IMD housing. The pin hole allows the gas applied in a hermeticity test that passes through defects in the feedthrough insulator or its attachment to the feedthrough pin or ferrule to be passed in a continuous gas pathway extending from the air space through the ferrule to gas detection equipment.

The gas pathway bypassing the filter element comprises one or more gap extending alongside and between the filter element and the ferrule. Any of the gas applied in a hermeticity test that passes through defects in the feedthrough insulator or its attachment to the feedthrough pin or ferrule passes in a continuous gas pathway extending from the air space alongside the washer and the filter element. The insulative barrier or spacer is preferably dimensioned to ensure a gas pathway bypassing it and may constitute a pre-formed insulative washer having an edge spaced at least in part from the ferrule sufficiently to allow gas passage. Any gas applied in a hermeticity test and passing through defects in the feedthrough insulator or its attachment to the feedthrough pin or ferrule into the air space is not blocked by the washer or spacer.

The pre-formed insulative washer provides an insulation layer of the lower, inner surface of the high dielectric capacitive filter or filter array and restrains flow of adhesive into the space between the filter element and the insulator to void blocking the passage of leak test gas and enabling hermeticity leak testing within a practical elapsed time.

The filter element preferably comprises a discoidal capacitor. Filtered feedthroughs and feedthrough arrays of the present invention can be employed in both high voltage and low voltage applications, and can be greatly miniaturized. The filtered feedthrough arrays or multi-polar capacitive filter arrays of the present invention can take any form including linear arrays and two-dimensional arrays.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

Figure 1:
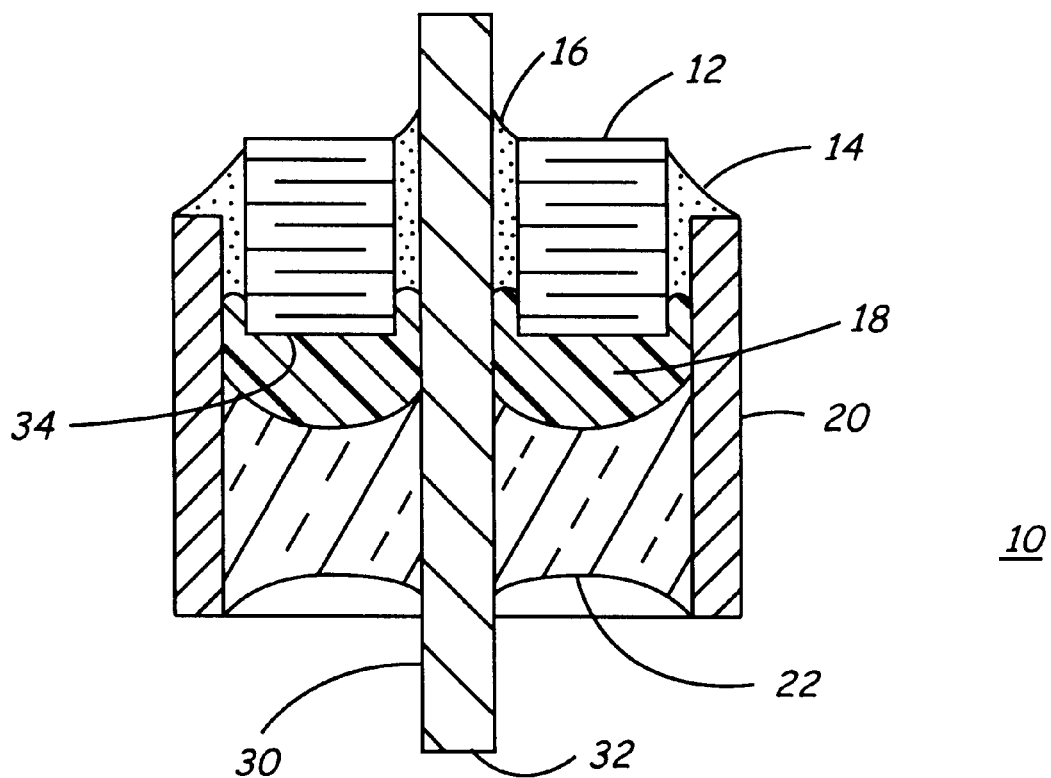
FIG. 1 is a side cross-section view of a representative prior art discoidal filtered feedthrough.

FIG. 1 illustrates a conventional prior art filtered feedthrough 10 incorporating a discoidal capacitive filter of the types described in the above-referenced, commonly assigned '551 patent. The feedthrough comprises a metallic ferrule 20, which may be employed to mount the feedthrough through the metallic housing of an IMD. A conductive pin 30 extends through an insulator 22, and serves to connect circuitry within an IMD to the exterior of the device. Typically, the exterior end 32 of pin 30 is coupled to one or more connector blocks employed to couple the IMD to an electrical lead or sensor of some sort as described above.

A discretely formed discoidal capacitor 12 is incorporated into the feedthrough 10 by use of conductive adhesive 14, 16 and non-conductive adhesive 18. The discoidal capacitor 12 is typically formed of a number of washer shaped layers or substrates of high dielectric barium titanate that are stacked together in a cylindrical, discoidal shape. Capacitor electrodes are deposited on the substrate surfaces in a first pattern that extends only to the outer edge of the washer shaped layer or in a second pattern that extends only to an inner through-hole or the substrate. The alternate patterned substrates are stacked together in the cylindrical shape to form overlapping, opposite polarity, capacitor electrodes. The number, sizes, spacing and overlapping relation of the discoidal capacitor electrodes varies in accordance with the desired capacitance value of the discoidal capacitor. The discoidal capacitor layers are typically formed of platinum, silver thick films, silver-palladium alloy thick films, or silver-platinum alloy thick films.

The discoidal capacitor electrodes that extend to the through-hole cylindrical surface of the stacked substrates are electrically connected together by a conductive metal layer that is deposited or otherwise formed around and over the inner through-hole cylindrical surface that thereby provides a first termination or pole of the discoidal capacitor for attachment to the feedthrough pin 30. Similarly, the discoidal capacitor electrodes that extend to the outer cylindrical surface of the stacked substrates are electrically connected together by a conductive metal layer that is deposited or otherwise formed around and over the outer cylindrical surface that thereby provides a second termination or pole of the discoidal capacitor for attachment to the ferrule 20 via conductive adhesive 16. The fabrication of the discrete discoidal capacitor 12 is then completed and it is ready to be attached electrically and mechanically to the feedthrough pin 30 and ferrule 20.

In the typical fabrication of a discoidal capacitive filtered feedthrough 10, the non-conductive insulator 22, pin 30 and ferrule 20 are first assembled together to form a feedthrough sub-assembly that is hermetically sealed. The insulator 22 and its attachment to the pin 30 and ferrule 20 can take any of the known forms including in situ formation of a glass seal from molten glass or the attachment by brazing of a ceramic insulator pre-form to the pin 30 and ferrule 20 using brazing pre-forms that are heated to melt the pre-forms.

After the feedthrough sub-assembly is formed, a predetermined amount of viscous non-conductive adhesive 18 is deposited above the upper surface of the insulator 22, and the discoidal capacitor 12 is inserted over the pin 30 and into the is ferrule 20. After the non-conductive adhesive 18 solidifies, conductive adhesives 14 and 16 (or a solder or the like) are applied to make the electrical connections with the first and second poles of the discoidal capacitor 12. The conductive adhesive 16 typically extends around the entire periphery of the pin 30 and fills the entire space between the pin 30 and the pole or termination of the discoidal capacitor 12 that the pin 30 is fitted through. The conductive adhesive 14 typically extends around the entire circumference of the ferrule 20, filling the entire space between the second termination or pole of capacitor 12 and the inner surface of ferrule 20. Centrifugal force may be required to drive the conductive adhesive 16 into the small gap between the feedthrough pin 30 and the inner hole surface of the discoidal capacitor 12. The conductive adhesives solidify to form these components into an integral feedthrough 10.

The use of the internally disposed non-conductive adhesive 18 in feedthroughs 10 certified for high voltage application ensures that no electrical arcing can take place between the feedthrough pin 30 and the outside diameter surface of the discoidal capacitor 12 or the inner end surface 34 of the discoidal filter 12. The internally disposed non-conductive adhesive 18 makes the assembly more durable and also prevents inward migration of the conductive epoxies 14 and 16 which could cause a short circuit between the ferrule 20 and pin 30. Consequently, this construction and fabrication technique is also used for low voltage certified feedthroughs and feedthrough arrays.

In the construction as illustrated in FIG. 1, it is not possible to easily leak test the feedthrough 10, due to the fact that the conductive and non-conductive adhesives 14, 16, 18 together effectively seal the entire upper, interior surface of the insulator 22 and that portion of the pin 30 and ferrule 20 which adjoin that insulator surface. However, this sealing of a defect in the insulator 22 or its attachment to the ferrule 20 or pin 30 can eventually fail to prevent infiltration of fluids through the feedthrough 10 and into the IMD housing over the years of implantation. Fluids will penetrate conductive and non-conductive epoxy adhesives and the epoxy connector of the IMD they are exposed to over years of implantation in the body. So, it is necessary to retain the use of the insulator 22 that is either formed in situ or brazed between the feedthrough pin 30 and ferrule 20 and provides a fluid barrier as long as the insulator 22 (and the braze, when used) is intact. It is preferable to be able to determine whether there is a defect in the insulator 22 or its attachment to the ferrule 20 or pin 30 before it is attached to an IMD and implanted in a patient.

FIGS. 2–9 show three embodiments of discoidal capacitive filtered feedthroughs or feedthrough arrays of the present invention having a gas bypass extending from the upper surface of the insulator and braze fixing the insulator between the feedthrough ferrule and pin and at least one gap extending between the capacitive filter or filter array and the ferrule interior wall to the upper surface thereof. FIG. 10 depicts an alternative embodiment having at least one leak test gas bypass hole extending through the ferrule wall to the space between the lower surface of the capacitive filter or filter array and the upper surface of the insulator and braze. It will be understood that the leak test gas bypass hole(s) can be substituted for the gap(s) in any of the feedthrough configurations of FIGS. 2–9.

Figure 2:
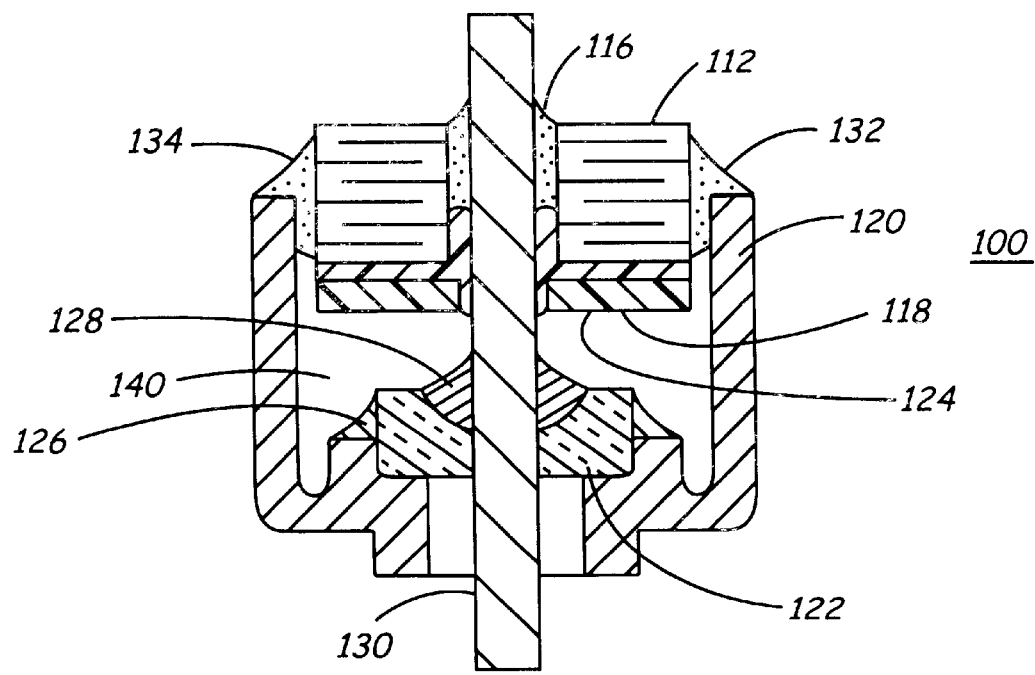
FIG. 2 is a side cross-section view taken along line 2—2 of FIG. 4 of a first embodiment of a discoidal filtered feedthrough in accordance with the present invention.
Figure 4:
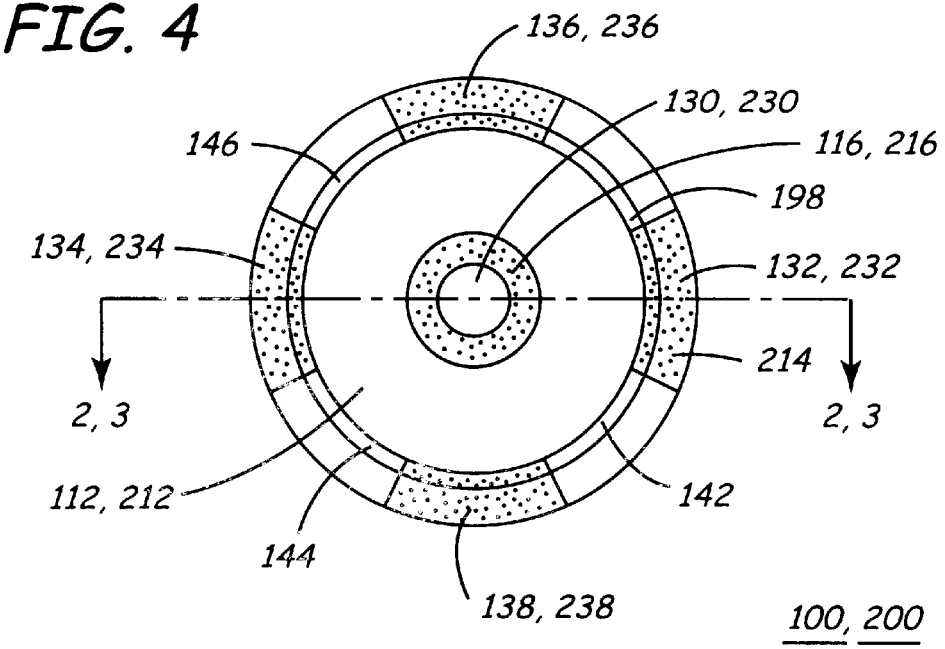
FIG. 4 is a top plan view of the filtered feedthroughs illustrated in FIGS. 2 and 3.
Figure 5:
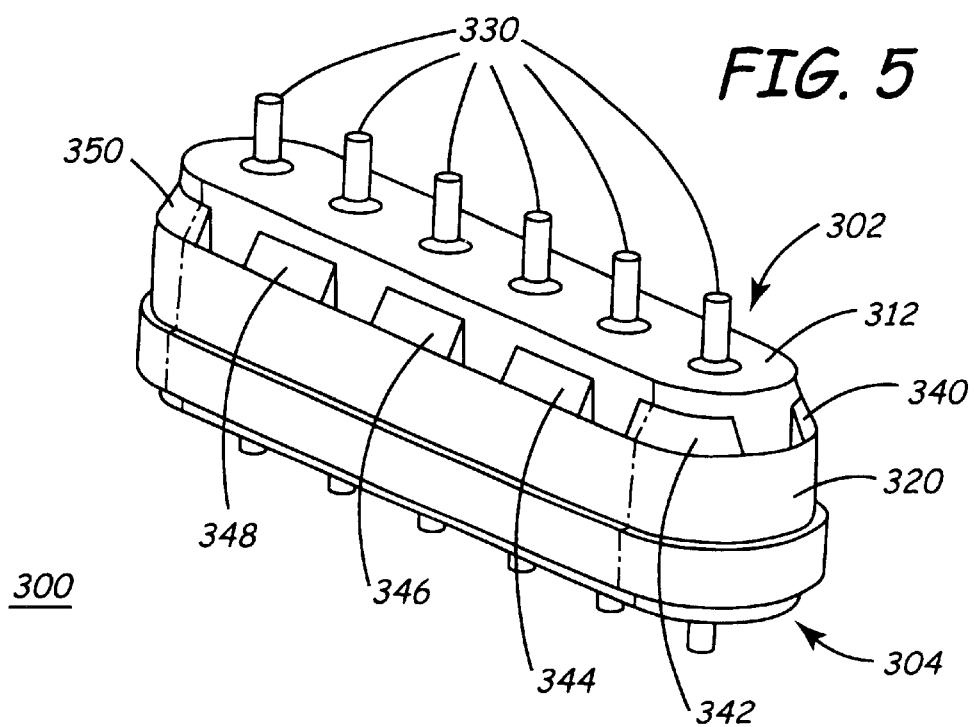
FIG. 5 is a perspective view of a filtered feedthrough array of a further embodiment of the present invention adapted to be fitted into an opening of a housing of a hermetically sealed electronic device showing the internally disposed portion configured to be disposed inside the housing and to face inward.

FIGS. 2 and 4 illustrate a first embodiment of a capacitive filtered feedthrough 100 according to the present invention incorporating a discoidal capacitor 112 above the insulator 122 and the use of pre-formed non-conductive spacer or washer 124. The conductive feedthrough pin 130 extends through a central hole in insulator 122, mounted to conductive ferrule 120 and a central hole in discoidal capacitor 112 also mounted to conductive ferrule 120. The insulator 122 is coupled to the ferrule 120 and the conductive feedthrough pin 130 by means of annular brazing pre-forms 126 and 128, respectively, to form a non-filtered feedthrough sub-assembly.

During fabrication, the non-conductive spacer or washer 124 is inserted over the pin 130 and between the facing end surfaces of the discoidal filter 112 and the insulator 122. The inner hole diameter is sized with respect to the outer diameter of the feedthrough pin 30 so that the washer 124 fits snugly against the feedthrough pin 130. Viscous non-conductive adhesive or a non-conductive epoxy pre-form that melts when heated is applied over the upper surface of the washer 124, and the discoidal capacitor is fitted over the feedthrough pin 130 and inside the ferrule 120. The inner or lower surface of the discoidal capacitor 112 then is adhered via the non-conductive adhesive 118 to the washer 124. It is important that the non-conductive adhesive 118 employed to mount the discoidal capacitor 112 to the spacer 124 is limited in volume so that it does not extend radially outward to make contact with the inner surface of the ferrule 120 around its entire periphery.

As illustrated, the spacer 124 takes the form of a washer with a centrally located hole to receive the feedthrough pin 130. The outer diameter of the spacer 124 is dimensioned such that its edge or at least a portion of its edge does not contact the inner surface of the ferrule 120, thereby leaving an opening or passage by the disk edge. Other configurations are also possible including configurations in which portions of the outer periphery or edge of the spacer 124 engage the inner surface of the ferrule 120. For purposes of the present invention, it is important simply that the spacer 124 is provided with a gas passing bypass around or through it. For example, the spacer outer diameter can be specified to be slightly less than the ferrule inner diameter so that its edge does not firmly engage the inner wall of ferrule 120. The spacer edge can also be shaped in whole or in part with gas pathways that are not blocked by the non-conductive adhesive 118.

After the non-conductive adhesive 118 solidifies, one pole of the discoidal capacitor 112 is coupled to the pin 130 by means of conductive solder or adhesive 116, corresponding generally to the interconnection of the discoidal capacitor 12 to the pin 30 in FIG. 1. Centrifugal force can be applied to drive the conductive adhesive 116 into the gap above the non-conductive adhesive 118.

In this embodiment of the invention, the conductive adhesive that couples the interior surface of the ferrule 120 to the exterior second pole or termination of the discoidal capacitor 112 does not extend around the entire circumference of the opening of the ferrule 120. Instead, at least one and preferably a plurality of gas bypasses are provided through the conductive adhesive and to the space 140 for helium gas to pass through if the insulator 122 or its braze via brazing pre-form 126 to the ferrule 120 or braze via brazing pre-form 128 to pin 130 is not hermetic.

FIG. 4 shows a plurality, e.g., four, openings or gaps 142, 144, 146, 148 between a like plurality of adhesive segments 132, 134, 136 and 138. The gaps 142, 144, 146, 148, between the outer surface of capacitor 112 and the inner surface of ferrule 120 define a gas flow passage that extends from the upper, inner surface of insulator 122 to the upper exterior of the feedthrough 100. Of course, at least one gap would be sufficient, but any number of gaps can be provided, and the gap(s) can be minute in cross-section and not visible to the eye. In high voltage applications, the upper surface of the discoidal capacitor 112 is typically insulated with a non-conductive material, e.g., a non-conductive epoxy or polyimide that does not extend into the gap(s).

It is possible to leak test the capacitive filtered feedthrough 100 because the upper, inner surface of insulator 122 is not sealed by non-conductive adhesive and because the pathway is provided between the outer circumference of capacitor 112 and the inner surface of ferrule 120. Any gas which passes through the assembly of the ferrule 120, insulator 122, pin 130, and the braze effected by melting of the brazing preforms 126 and 128 in situ may readily pass through the assembly by means of the gaps between the outer edge of the spacer 124, and the inner surface of ferrule 120 and between the outer surface of discoidal capacitor 112 and the inner surface of ferrule 120.

Figure 3:
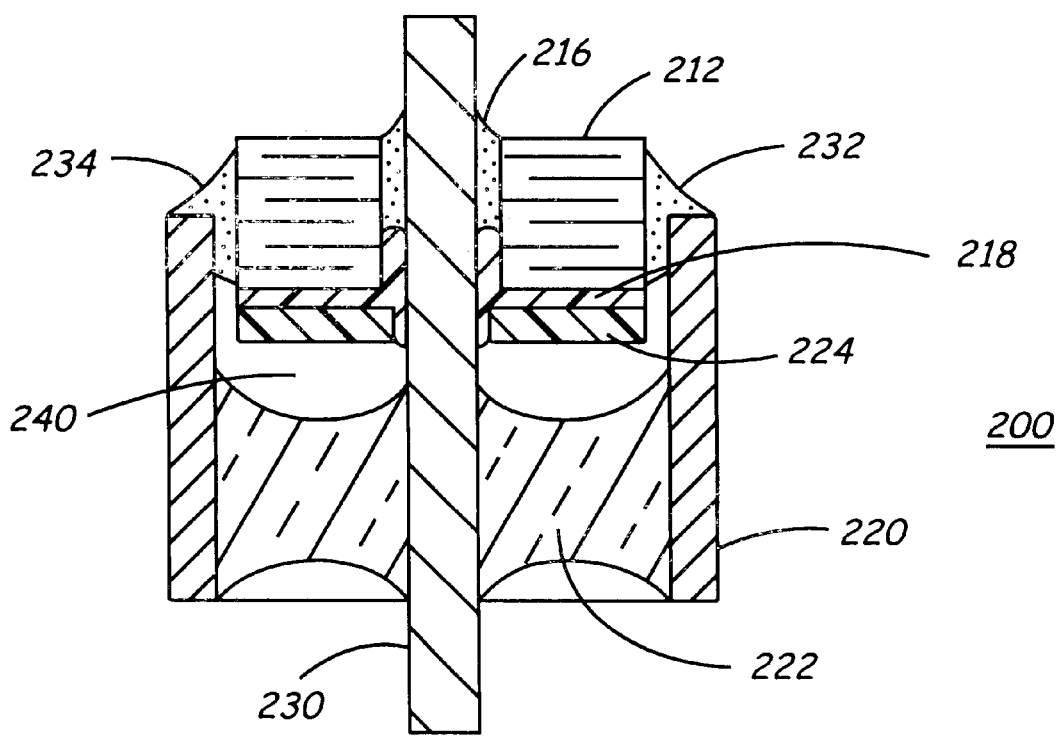
FIG. 3 is a side cross-section view taken along line 3—3 of FIG. 4 of a second embodiment of a discoidal filtered feedthrough in accordance with the present invention.

FIGS. 3 and 4 illustrate a second embodiment of a capacitive filtered feedthrough 200 according to the present invention. In this embodiment, the feedthrough 200 includes a conductive ferrule 220, an insulator 222, a conductive pin 230, and a discoidal capacitor 212 corresponding generally to conductive ferrule 120, insulator 122, pin 130, and discoidal capacitor 112 of FIG. 1. The first pole of the discoidal capacitor 212 is coupled to the conductor pin 230 by a conductive adhesive 216. However, like the embodiment of FIGS. 2 and 4, the feedthrough 200 is fabricated with an insulative spacer or washer 224 coupled to the lower, interior surface of the discoidal capacitor 212 by a non-conductive adhesive 218. The insulative washer outer diameter is smaller than the inner diameter of the ferrule 220 or otherwise configured as described above with respect to washer 124, thereby providing a gap for the passage of leak test gas. And, again, the conductive adhesive coupling the second pole of the discoidal capacitor 212 to the ferrule 220 is formed preferably with at least one gap providing a gas pathway from the interior space 240 of the feedthrough 200 providing a gas pathway which bypasses the discoidal capacitor 212 and allows the feedthrough 200 to be readily leak tested after fabrication is completed.

The coupling of the discoidal capacitor 212 to ferrule 220 as illustrated in the top plan view in FIG. 4 provides for a plurality, e.g., four openings or gaps 242, 244, 246, 248 between four discrete adhesive segments 232, 234, 236, 238. The gaps 242, 244, 246, 248, between the outer surface of capacitor 212 and the inner surface of ferrule 220 define a gas flow passage that extends from the upper, inner surface of insulator 222 to the upper exterior of the feedthrough 200. Of course, at least one gap would be sufficient, but any number of gaps can be provided, and the gap(s) can be minute in cross-section and not visible to the eye.

FIGS. 5–9 illustrate the application of the principles of the present invention to a filtered feedthrough array 300 constituting several filtered feedthrough pins 330 supported within a common ferrule 320 by a plurality of insulators 322. The feedthrough array 300 has an internally disposed portion 302 that is disposed inside the IMD housing and an externally disposed portion 304 that is disposed outside the IMD housing when the elongated flange 320 is welded or affixed to an opening in the IMD housing.

Again, the preferred filter element for each feedthrough pin 330 comprises a discoidal capacitor, and a plurality of discoidal capacitors are formed in a capacitor array 312 having a shape that fits within the elongated ferrule 320. The discoidal capacitor array 312 includes a number, six in this example, of pin through-holes that the feedthrough pins 330 extend through. The discoidal capacitor array 312 is formed to have a like number of electrically isolated discoidal capacitors each formed of a plurality or capacitor plates extending outwardly from a first hole or termination of each pin through-hole and a plurality of capacitor plates extending to a common second pole or termination. Each electrically isolated capacitor first pole is electrically and mechanically attached to a separate feedthrough pin 330. The common capacitor second pole or termination is electrically and mechanically coupled to the ferrule 320.

Although a discoidal capacitor array 312 is depicted having six integrally formed capacitive filters, it will be understood that a plurality of discretely formed discoidal capacitors could be employed instead that are each inserted into a ferrule having discrete cylindrical walls for receiving the discretely formed discoidal capacitors.

Figure 9:
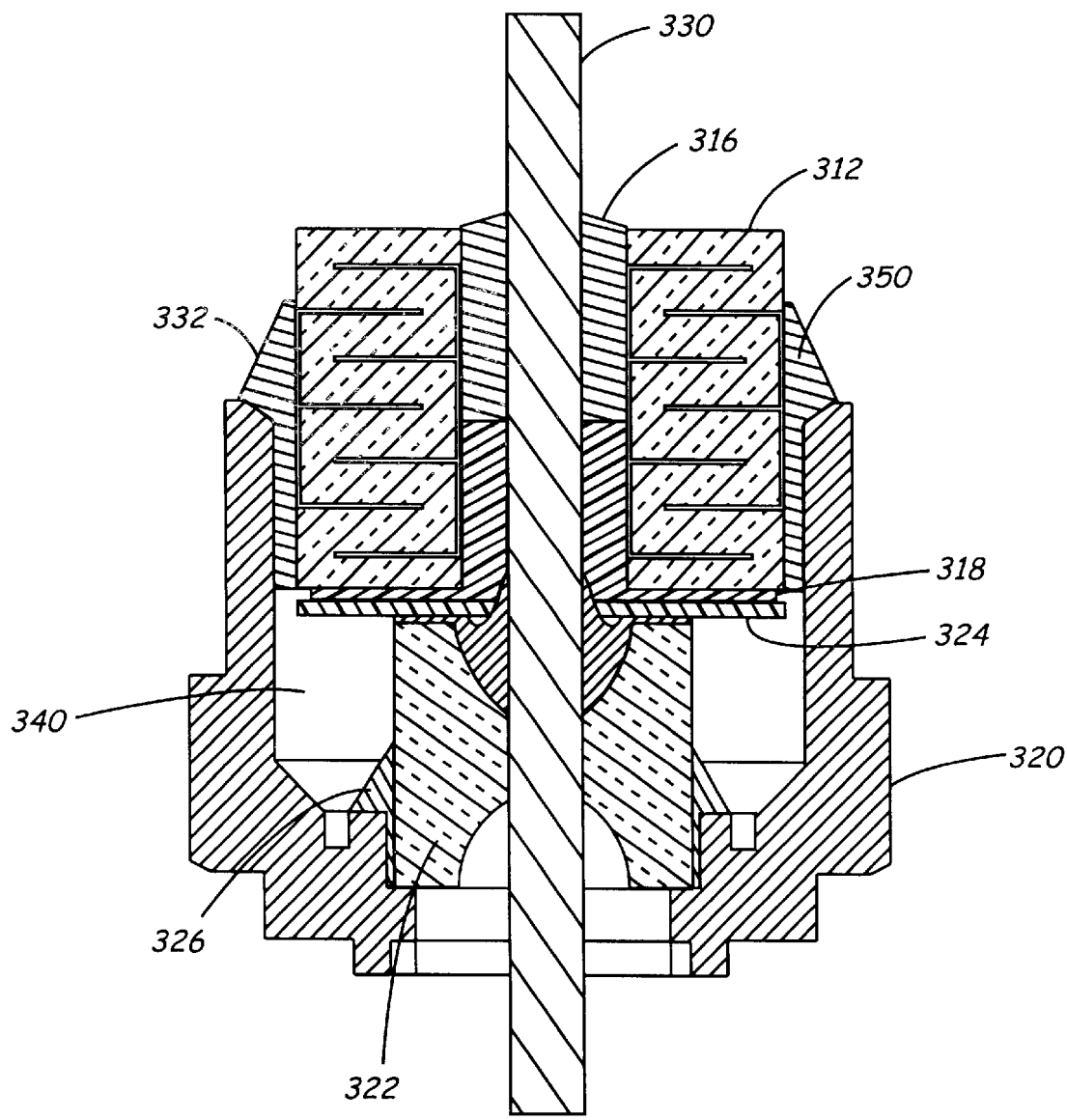
FIG. 9 is an expanded end cross-section view of one filtered feedthrough sub-assembly of the filtered feedthrough array of FIG. 5.
Figure 10:
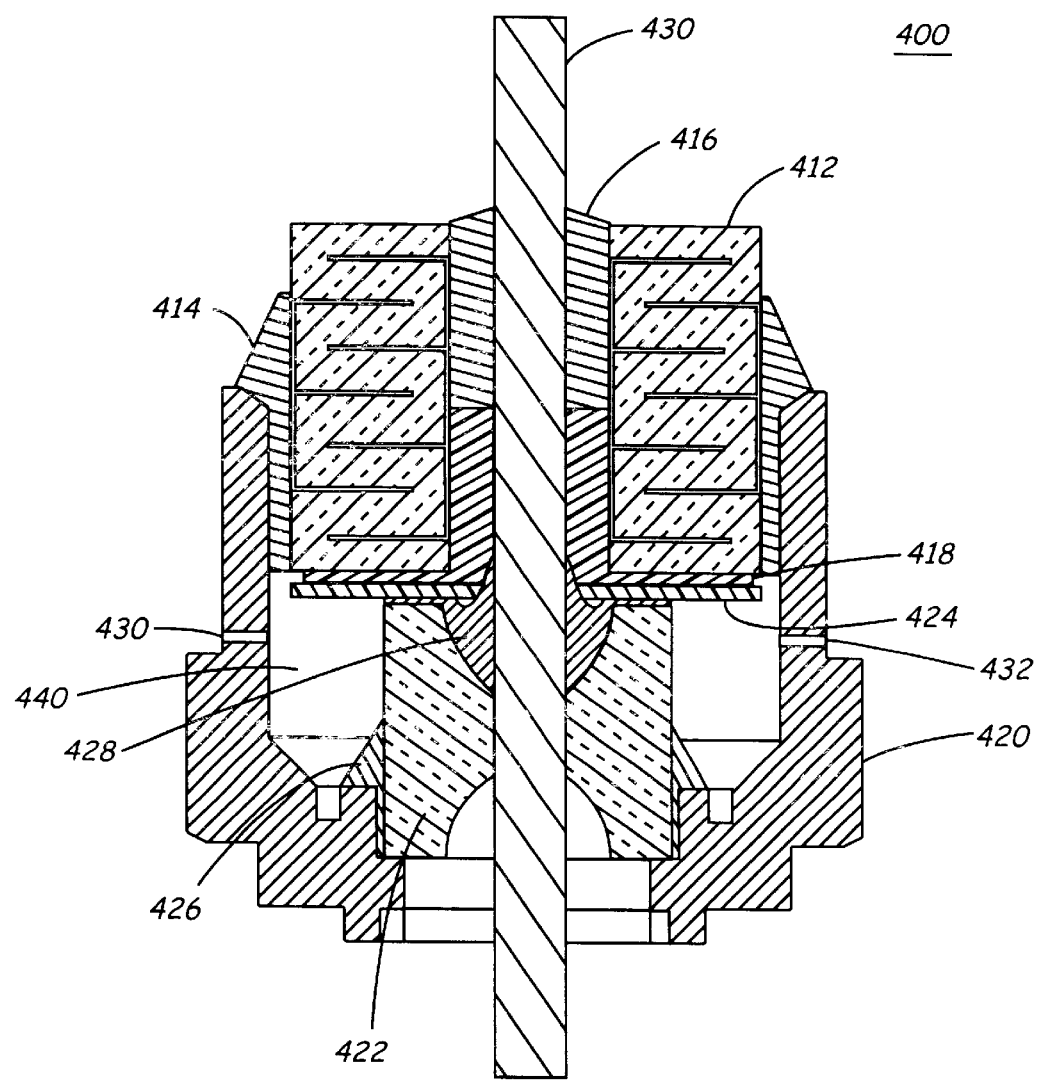
FIG. 10 is an expanded cross-section view of a further embodiment of the invention providing a leak test gas bypass hole through the side wall of the feedthrough ferrule.

One of the feedthroughs of the filtered feedthrough array 300 is shown in the end cross-section view of FIG. 9. Each feedthrough pin 330 is separately supported by its own cylindrical insulator 322 that is mechanically attached to a circular recess of the ferrule 320 employing a brazing pre-form 326. Each feedthrough pin 330 is brazed to its cylindrical insulator 322 employing a brazing pre-form 328. Each feedthrough pin 330 extends though an aligned hole centered about a discoidal capacitor of the discoidal capacitor array 312.

A separate insulating washer 324 is fitted over the upper surface of each insulator 322 and the pin-insulator braze joint after the braze pre-forms 326 and 328 are melted to braze the feedthrough pins 330 and insulators 322 together and to the ferrule 320. The washers 324 are dimensioned in diameter so that the washer edges are spaced from the interior side wall of the ferrule 320 (or otherwise configured as described above with respect to washer 124) providing the gap for passage of helium gas that may pass through defects of the insulator or the braze joints with the feedthrough pins 330 and with the ferrule 320 as shown in FIG. 9.

Although a plurality of separate insulating washers 324 are depicted, it will be understood that a single pre-formed washer or separator having multiple through-holes for receiving the conductive pins 330 could be substituted for the plurality of separate insulating washers 324.

The discoidal capacitor array 312 is fitted over the feedthrough pins 330 and into the ferrule 320, and the non-conductive adhesive 318 is applied into and partly fills the space between the feedthrough pins 330 and the holes in each discoidal capacitor of the discoidal capacitor array 312. A conductive adhesive 316 is then applied into the remaining space between the feedthrough pins 330 and the holes in each discoidal capacitor of the discoidal capacitor array 312 to make electrical and mechanical connections between the feedthrough pin 330 and the conductive termination on the side wall of the hole coupled to first sets of radially extending, parallel capacitive plates forming the first capacitor pole of each individual capacitor.

Although the insulating washer 324 is depicted as snugly fitting between braze 328 and the adhesive 318, it will be understood that helium leak test gas passing through a defect in the braze 328 can pass between the upper surface of the braze 328 and insulator 322 and the lower surface of washer 324 into the space 390.

Figure 6:
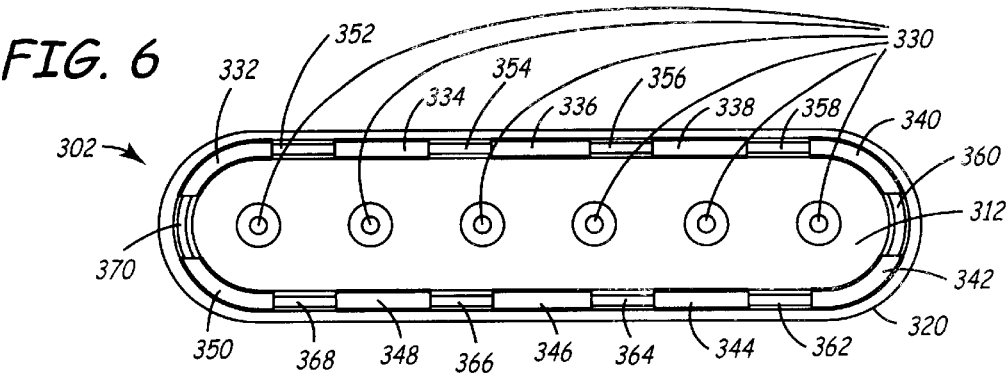
FIG. 6 is a top plan view looking toward the internally disposed portion of the filtered feedthrough array of FIG. 5.
Figure 7:
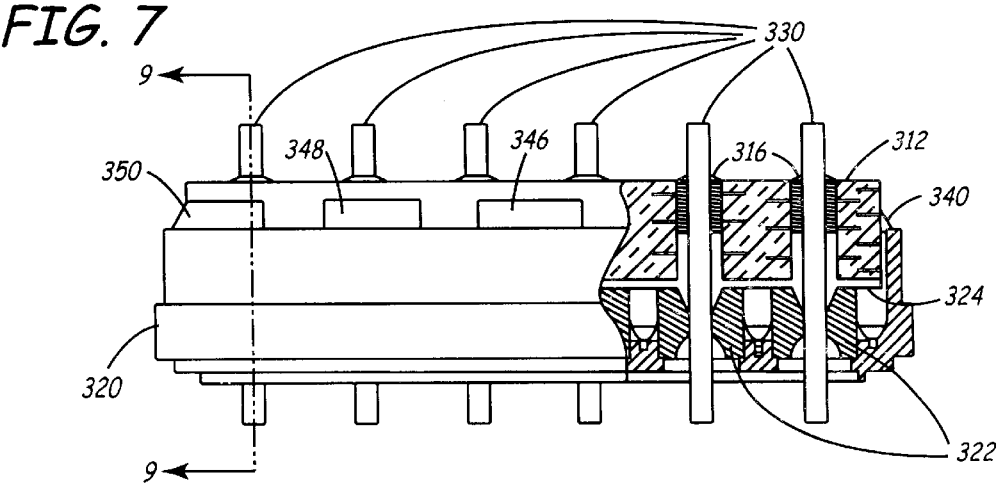
FIG. 7 is a partial cross-section side view of the filtered feedthrough array of FIG. 5.
Figure 8:
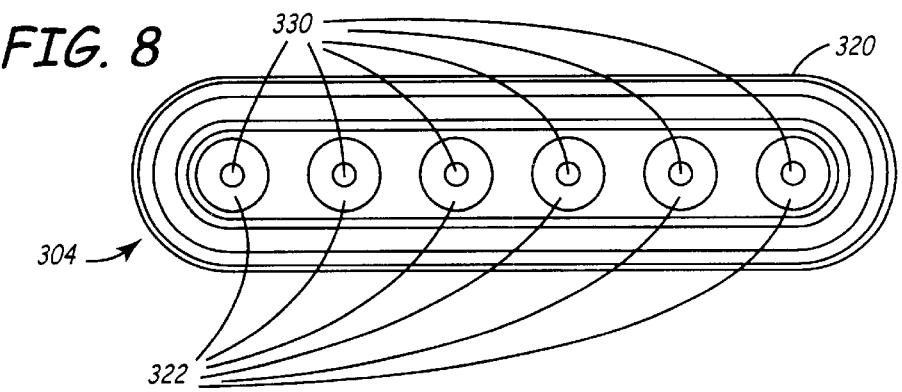
FIG. 8 is a bottom plan view looking toward the externally disposed portion of the filtered feedthrough array of FIG. 5.

As shown in FIGS. 6 and 7, a plurality of conductive segments 332, 334, 336, 338, 340, 342, 344, 346, 348, 350 extend between the conductive termination on the exterior side wall of the discoidal capacitor array 312 that is coupled with a second set of radially extending, parallel capacitive plates forming the second capacitor pole of each capacitor that are all electrically connected in common. A like plurality of gaps 352, 354, 356, 358, 360, 362, 364, 366, 368, 370 are formed between the plurality of conductive segments 332, 334, 336, 338, 340, 342, 344, 346, 348, 350 that function as pathways for passage of helium gas that may pass through defects of the insulator or the braze joints with the feedthrough pins 330 and with the ferrule 320.

In the above-described embodiments, the spacer 124, 224, 324 is depicted as a washer having a centrally disposed opening so that it can be fitted over the feedthrough pin 130, 230, 330 and a diameter smaller than the inner diameter of the cylindrical ferrule 120, 220 or the distance between the inner surfaces of the elongated side walls of ferrule 320, thereby providing a gap that is part of the pathway for gas. It will be understood that the diameter or width of the spacer 124, 224, 324 can be increased so that the spacer edge does contact the inner surface of the ferrule. In that case, it may be necessary to provide holes through the spacer 124, 224, 324 or to scallop or notch the edges of the spacer 124, 224, 324 to provide at least one notched gap. The spacer 124, 224, 324 provides electrical insulation of the discoidal capacitor inner end surface from electrical arcing.

For applications with N filter feedthroughs, a single insulator and/or spacer may be used with up to N holes. A single insulator and/or spacer will improve manufacturability since fewer parts will need to be assembled. Higher pin density (i.e., tighter pin to pin spacing) may also be achieved by using a single insulator with N holes.

In the above-described embodiments, a discoidal capacitor 112, 212 or discoidal capacitor array 312 is provided that is attached between the feedthrough pin(s) 130, 230, 330 and ferrule 120, 220, 320. It will be understood that the present invention may be employed in a filtered feedthrough or feedthrough array wherein other resistive or inductive filter elements are employed instead of or in addition to a capacitive filter.

The practice of the present invention is not specific to any particular materials used for the various components. The non-conductive adhesive 118, 218, 318 may be an epoxy (paste or performed) or any other polymeric non-conductive adhesive such as Ablestick 789-3 adhesive provided by ABLESTIK LABORATORIES of Rancho Dominguez, Calif. The purpose of the non-conductive adhesive is to prevent migration of the conductive adhesive and to prevent the surface of the discoidal capacitor 112, 212 or the discoidal capacitor array 312 from arcing in high voltage applications. The conductive adhesive 114, 214, 314 and 116, 216, 316 may be a conductive polyimide adhesive. One example of an appropriate conductive adhesive is Ablestick 8700E or ABLEBOND.RTM. 8700 electrically conductive silver-filled epoxy adhesive provided by ABLESTIK LABORATORIES of Rancho Dominguez, Calif. The ferrule 120, 220, 320, may be formed of a conductive material selected from the group consisting of stainless steel, niobium, titanium, titanium alloys such as titanium-6Al-4V or titanium-vanadium, tantalum, and alloys, mixtures and combinations thereof. The insulator 122, 222, 322 and conductive pin 130, 230, 330 may be any of the various known materials typically employed in the manufacture of feedthroughs. The spacer 124, 224, 324 may be fabricated of polymeric materials, e.g., polyimide.

Within the context of the present invention, modifications to the designs illustrated are believed workable. For example, rather than employing conductive adhesive to attach the filter capacitor to the feedthrough pin, the hole or holes of the filter element may instead be soldered to the feedthrough pin.

In an further alternative embodiment, the spacer 124, 224, 324 may be retained without the use of a non-conductive polymeric adhesive 118, 218, 318.

In this case, the conductive adhesive or solder 116, 216, 316 employed to couple the pin 130, 230, 330 to the filter capacitor hole must be chosen such that no excess conductive material will flow onto the spacer 124, 224, 324. In this context, there should be sufficient mechanical interference between the through-hole of the spacer 124, 224, 324 and the pin 130, 230, 330 to control the wetting of the conductive polymeric adhesive or solder 116, 216, 316, preventing it from flowing onto the surface of the spacer 124, 224, 324.

In the context of the present invention, substantial variation is possible, so long as a continuous gas flow path is provided from the upper surface of the insulator to the exterior of the feedthrough, bypassing the discoidal capacitor or other filter element and the spacer that insulates its lower surface. In the embodiments of the present invention illustrated in FIGS. 2–9 and described above, this gas flow path is provided by means of one or more opening or gap between the outer cylindrical surface of the discoidal capacitor and the ferrule and the outer surface of the spacer and the ferrule. It can be envisioned, however, that the gas flow path or pathway bypassing the filter element can in some cases be reversed by providing corresponding gaps between the feedthrough pin and the inner surface of the through-hole of the filter element. While such an embodiment is believed to be substantially more difficult to manufacture, the reversal of the elements of the illustrated embodiments of the feedthrough is also believed to be within the scope of the present invention.

FIG. 10 depicts the alternative embodiment of the invention of a feedthrough or feedthrough array 400 having at least one leak test gas bypass hole 430 and/or 432 extending through the wall of ferrule 420 to the air space 440 between the lower surface of the capacitive filter or filter array 412 and the upper surface of the insulator 422 and braze 426 and 428. In this embodiment, the bypass holes 430, 432 extend from the air space 440 and at any location above the weld flange surface used for laser welding or otherwise hermetically attaching the feedthrough ferrule 420 to the IMD housing so that they are not blocked in the attaching process. The same processing steps are followed as described above for disposing the washer 424 between the non-conductive adhesive 418 and braze 428 and for otherwise assembling the capacitive filtered feedthrough 400, except that no leak test gas bypass gaps need be formed in the conductive adhesive or solder 414. Instead, the conductive adhesive or solder 414 preferably extends completely around the outer surface of the capacitive filter 412 and to the inner wall of the ferrule 420.

Typically, the ferrule of the feedthrough or feedthrough array is welded to a metallic enclosure or housing of an IMD to complete the hermetic seal of components located within the enclosure. At times, the stresses caused by the welding step can fracture the insulator. The provision of the gas flow pathway that remains open after welding the ferrule to the opening of the housing of the IMD enables post-weld helium leak testing of the insulator.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. A leak testable, filtered electrical feedthrough, comprising:
    an insulator having an insulator through-hole extending between an upper insulator surface and a lower insulator surface and having an outer insulator surface;
    a conductive feedthrough pin extending through the insulator through-hole and hermetically sealed with the insulator;
    a conductive ferrule having a ferrule inner wall hermetically sealed with and surrounding the outer insulator surface;
    a filter element fitted between and electrically attached with said feedthrough pin and said conductive ferrule above said insulator and having an upper filter element surface and a lower filter element surface spaced apart from said upper insulator surface;
    a non-conductive, pre-formed spacer fitted within an interior space between said lower filter element surface and said upper insulator surface and about said feedthrough pin that electrically insulates the lower filter element surface and separates it from the insulator; and
    means for providing a gas pathway extending from said interior space to the exterior of said filtered electrical feedthrough bypassing said filter element,
    whereby leak test gas applied to said lower insulator surface and passing through defects in said insulator is passed through the gas pathway bypassing said filter element to enable a determination that the insulator is not hermetically sealed.

2. The feedthrough of claim 1, wherein the filter element further comprises a discoidal capacitor located above the inner surface of the insulator, the discoidal capacitor having a through-hole extending between upper and lower discoidal capacitor surfaces that receives and is electrically connected with said feedthrough pin and an outer peripheral surface that is coupled to the ferrule by conductive material interposed between the filter element outer peripheral surface and the ferrule.

3. The feedthrough of claim 2, wherein the means for providing a gas pathway extending from said interior space bypassing said discoidal capacitor comprises at least one gap in the conductive material interposed between the discoidal capacitor outer peripheral surface and the ferrule, the gap extending between the interior space and the upper discoidal capacitor surface.

4. The feedthrough of claim 3, wherein the means for providing a gas pathway extending from said interior space comprises a configuration of said spacer to provide a gas pathway between said ferrule and an outer edge of said spacer for passing gas past said spacer to said at least one gap.

5. The feedthrough of claim 1, wherein the means for providing a gas pathway extending from said interior space comprises a leak test gas passing hole extending through the side wall of the feedthrough ferrule to said interior space for providing a gas pathway extending from said space and bypassing said filter element,
    whereby gas applied to said lower insulator surface and passing through defects in said insulator and reaching said interior space is passed through said leak test gas passing hole and can be detected to determine that the insulator is not hermetically sealed.

6. The feedthrough of claim 1, wherein:
    said filter element has a through-hole extending between upper and lower filter element surfaces that receives and is electrically connected with said feedthrough pin and an outer peripheral surface that is coupled to the ferrule by conductive material interposed between the filter element outer peripheral surface and the ferrule; and
    the means for providing a gas pathway extending from said interior space bypassing said filter element comprises at least one gap in the conductive material interposed between the filter element outer peripheral surface and the ferrule, the gap extending between the upper filter element surface and the lower filter element surface.

7. A leak testable, filtered electrical feedthrough, comprising:
    a feedthrough conductor;
    an insulator surrounding the feedthrough conductor and having an upper, inner surface;
    a conductive ferrule surrounding the insulator;
    a filter element located above the inner surface of the insulator, the filter element having a through-hole extending between filter element upper and lower surfaces and receiving the feedthrough conductor and having an outer peripheral surface extending between the filter element upper and lower surfaces and coupled with the ferrule;
    a pre-formed, nonconductive spacer fitted between the filter element lower surface and the insulator upper, inner surface; and
    means for providing a gas flow path extending from the upper surface of the insulator to the exterior of the feedthrough bypassing the filter element and the pre-formed, nonconductive spacer, whereby gas applied to said lower insulator surface and passing through defects in said insulator is passed through the gas pathway of said spacer and the gas pathway extending from said spacer and bypassing said filter element to enable a determination that the insulator is not hermetically sealed.

8. The feedthrough of claim 7, wherein the means for providing a gas pathway extending from said interior space bypassing said filter element comprises at least one gap between the outer peripheral surface of said filter element and the inner surface of said ferrule.

9. A filtered electrical feedthrough array of N filtered feedthroughs, comprising:

a conductive ferrule having as ferrule interior surface;

a plurality N of feedthrough conductors;

a plurality N of insulators mounted at spaced apart locations to said ferrule interior surface, each insulator surrounding a feedthrough conductor and having an upper, inner surface;

a plurality N of filter elements each located above the inner surface of the insulator, each filter element having a through-hole extending between filter element upper and lower surfaces and receiving a feedthrough conductor and having an outer peripheral surface extending between the filter element upper and lower surfaces and coupled with the ferrule in relation to an insulator;

a plurality N of pre-formed, nonconductive spacers each fitted in an interior space between a filter element lower surface and an insulator upper, inner surface, whereby N filtered feedthroughs are formed at separated locations of said ferrule; and means for providing a gas pathway extending from said interior space to the exterior of said filtered electrical feedthrough bypassing said filter element, whereby leak test gas applied to said lower insulator surface and passing through defects in any of said insulators is passed through the gas flow path bypassing said filter elements to enable a determination that an insulator is not hermetically sealed.

10. The feedthrough of claim 9, wherein each filter element further comprises a discoidal capacitor located above the inner surface of an insulator, the discoidal capacitor having a through-hole extending between upper and lower discoidal capacitor surfaces that receives and is electrically connected with a feedthrough pin and an outer peripheral surface that is coupled to the ferrule by conductive material interposed between the filter element outer peripheral surface and the ferrule.

11. The feedthrough of claim 10, wherein the means for providing a gas pathway extending from said interior space bypassing each discoidal capacitor comprises at least one gap in the conductive material interposed between the discoidal capacitor outer peripheral surface and the ferrule, the gap extending between the upper discoidal capacitor surface and the lower discoidal capacitor surface.

12. The feedthrough of claim 10, wherein the means for providing a gas pathway extending from said interior space comprises a configuration of said spacer to provide a gas pathway between said ferrule and an outer edge of said spacer for passing gas past said spacer to said at least one gap.

13. The feedthrough of claim 10, wherein the means for providing a gas pathway extending from said interior space comprises a leak test gas passing hole extending through the side wall of the feedthrough ferrule to said interior space for providing a gas pathway extending from said space and bypassing said capacitive filter, whereby gas applied to said lower insulator surface and passing through defects in any of said insulators and reaching said interior space is passed through said leak test gas passing hole and can be detected to determine that the insulator is not hermetically sealed.

14. The feedthrough of claim 9, wherein:

each filter element has a through-hole extending between upper and lower filter element surfaces that receives and is electrically connected with said feedthrough pin and an outer peripheral surface that is coupled to the ferrule by conductive material interposed between the filter element outer peripheral surface and the ferrule; and the means for providing a gas pathway extending from each spacer bypassing each filter element comprises at least one gap in the conductive material interposed between the filter element outer peripheral surface and the ferrule, the gap extending between the upper filter element surface and the lower filter element surface.

15. The feedthrough of claim 14, wherein the means for providing a gas pathway extending from said interior space bypassing each filter element comprises at least one gap in the conductive material interposed between the discoidal capacitor outer peripheral surface and the ferrule, the gap extending between the upper filter element surface and the lower filter element surface.

16. The feedthrough of claim 15, wherein the means for providing a gas pathway extending from said interior space comprises a configuration of said spacer to provide a gas pathway between said ferrule and an outer edge of said spacer for passing gas past said spacer to said at least one gap.

17. The feedthrough of claim 9, wherein the means for providing a gas pathway extending from said interior space comprises a leak test gas passing hole extending through the side wall of the feedthrough ferrule to said interior space for providing a gas pathway extending from said space and bypassing said filter element, whereby gas applied to said lower insulator surface and passing through defects in any of said insulators and reaching said interior space is passed through said leak test gas passing hole and can be detected to determine that the insulator is not hermetically sealed.

18. The feedthrough of claim 11, wherein:

each filter element has a through-hole extending between upper and lower filter element surfaces that receives and is electrically connected with a feedthrough pin and an outer peripheral surface that is coupled to the ferrule by conductive material interposed between the filter element outer peripheral surface and the ferrule; and the means for providing a gas pathway extending from each spacer bypassing each filter element comprises at least one gap in the conductive material interposed between the filter element outer peripheral surface and the ferrule, the gap extending between the upper filter element surface and the lower filter element surface.

19. A filtered electrical feedthrough, comprising:

an insulator having an insulator through-hole extending between an upper insulator surface and a lower insulator surface and having an outer insulator surface;

a conductive feedthrough pin extending through the insulator through-hole and hermetically sealed with the insulator;

a conductive ferrule having a ferrule inner wall hermetically sealed with and surrounding the outer insulator surface;

a filter element fitted between and electrically attached with said feedthrough pin and said conductive ferrule above said insulator and having an upper filter element surface and a lower filter element surface spaced apart from said upper insulator surface providing an interior space;

a non-conductive, pre-formed spacer fitted within the interior space between said lower filter element surface and said upper insulator surface and about said feedthrough pin that electrically insulates the lower filter element surface and separates it from the feedthrough pin and insulator; and a leak test gas passing hole extending through the side wall of the feedthrough ferrule to said interior space for providing a gas pathway extending from said space and bypassing said filter element, whereby gas applied to said lower insulator surface and passing through defects in said insulator and reaching said interior space is passed through said leak test gas passing hole and can be detected to determine that the insulator is not hermetically sealed.

20. A filtered electrical feedthrough array of N filtered feedthroughs, comprising:

a conductive ferrule having as ferrule interior surface;

a plurality N of feedthrough conductors;

a plurality N of insulators mounted at spaced apart locations to said ferrule interior surface, each insulator surrounding a feedthrough conductor and having an upper, inner surface;

a plurality N of filter elements each located above the inner surface of the insulator, each filter element having a through-hole extending between filter element upper and lower surfaces and receiving a feedthrough conductor and having an outer peripheral surface extending between the filter element upper and lower surfaces and coupled with the ferrule in relation to an insulator;

a plurality N of pre-formed, nonconductive spacers each fitted in an interior space between a filter element lower surface and an insulator upper, inner surface, whereby N filtered feedthroughs are formed at separated locations of said ferrule; and a leak test gas passing hole extending through the side wall of the feedthrough ferrule to said interior space for providing a gas pathway extending from said space and bypassing said filter element, whereby gas applied to said lower insulator surface of said N insulators and passing through defects in any of said N insulators and reaching said interior space is passed through said leak test gas passing hole and can be detected to determine that an insulator is not hermetically sealed.

21. The N filtered feedthroughs of claim 20 wherein a single homogenous insulator is implemented.

22. The N filtered feedthrough of claim 20 wherein a single homogenous spacer is implemented.

* * * * *